(12) United States Patent
Clark

(10) Patent No.: US 7,425,659 B2
(45) Date of Patent: Sep. 16, 2008

(54) ALKYLAROMATICS PRODUCTION

(75) Inventor: Michael C. Clark, Pasadena, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 453 days.

(21) Appl. No.: 11/343,868

(22) Filed: Jan. 31, 2006

(65) Prior Publication Data

US 2007/0179329 A1    Aug. 2, 2007

(51) Int. Cl.
C07C 2/66    (2006.01)
(52) U.S. Cl. .................................... 585/467
(58) Field of Classification Search .................. 585/467
See application file for complete search history.

(56) References Cited

U.S. PATENT DOCUMENTS

| | | |
|---|---|---|
| 3,293,192 A | 12/1966 | Maher et al. |
| 3,308,069 A | 3/1967 | Wadlinger et al. |
| 3,354,078 A | 11/1967 | Miale et al. |
| 3,442,795 A | 5/1969 | Kerr et al. |
| 3,449,070 A | 6/1969 | McDaniel et al. |
| 3,524,820 A | 8/1970 | Hemminger |
| 3,702,886 A | 11/1972 | Argauer et al. |
| 3,709,979 A | 1/1973 | Chu |
| 3,751,504 A | 8/1973 | Keown et al. |
| 3,751,506 A | 8/1973 | Burress |
| 3,766,093 A | 10/1973 | Chu |
| 3,832,449 A | 8/1974 | Rosinski et al. |
| RE28,341 E | 2/1975 | Wadlinger et al. |
| 3,894,104 A | 7/1975 | Chang et al. |
| 3,923,636 A | 12/1975 | Mead et al. |
| 3,972,983 A | 8/1976 | Ciric |
| 4,016,218 A | 4/1977 | Haag et al. |
| 4,016,245 A | 4/1977 | Plank et al. |
| 4,076,842 A | 2/1978 | Plank et al. |
| RE29,948 E | 3/1979 | Dwyer et al. |
| 4,234,231 A | 11/1980 | Yan |
| 4,401,556 A | 8/1983 | Bezman et al. |
| 4,429,176 A | 1/1984 | Chester et al. |
| 4,439,409 A | 3/1984 | Puppe et al. |
| 4,522,929 A | 6/1985 | Chester et al. |
| 4,556,477 A | 12/1985 | Dwyer |
| 4,594,146 A | 6/1986 | Chester et al. |
| 4,663,492 A | 5/1987 | Chester et al. |
| 4,826,667 A | 5/1989 | Zones et al. |
| 4,891,458 A | 1/1990 | Innes et al. |
| 4,954,325 A | 9/1990 | Rubin et al. |
| 4,992,606 A | 2/1991 | Kushnerick et al. |
| 5,015,786 A | 5/1991 | Araki et al. |
| 5,077,445 A | 12/1991 | Le |
| 5,081,323 A | 1/1992 | Innes et al. |
| 5,149,894 A | 9/1992 | Holtermann et al. |
| 5,160,497 A | 11/1992 | Juguin et al. |
| 5,177,285 A | 1/1993 | Van Opdorp et al. |
| 5,191,135 A | 3/1993 | Dwyer et al. |
| 5,198,595 A | 3/1993 | Lee et al. |
| 5,236,575 A | 8/1993 | Bennett et al. |
| 5,250,277 A | 10/1993 | Kresge et al. |
| 5,258,565 A | 11/1993 | Kresge et al. |
| 5,324,877 A | 6/1994 | West et al. |
| 5,362,697 A | 11/1994 | Fung et al. |
| 5,371,310 A | 12/1994 | Bennett et al. |
| 5,453,554 A | 9/1995 | Cheng et al. |
| 5,998,684 A | 12/1999 | Ho et al. |
| 5,998,687 A | 12/1999 | Woodle et al. |
| 6,077,498 A | 6/2000 | Diaz Cabañas |
| 6,093,866 A | 7/2000 | Wang et al. |
| 6,512,153 B1 * | 1/2003 | Cappellazzo et al. ........ 585/467 |
| 6,525,234 B1 | 2/2003 | Dandekar et al. |
| 6,909,026 B2 | 6/2005 | Dandekar et al. |

FOREIGN PATENT DOCUMENTS

| | | |
|---|---|---|
| EP | 0 064 046 | 11/1982 |
| EP | 0 293 032 | 11/1988 |
| EP | 0 432 814 | 6/1991 |
| EP | 0 537 389 | 4/1993 |
| EP | 0 538 518 | 4/1993 |
| EP | 0 629 549 | 12/1994 |
| EP | 0 842 914 | 5/1998 |
| EP | 1 069 100 | 1/2001 |
| FR | 2662438 | 11/1991 |

(Continued)

OTHER PUBLICATIONS

"Atlas of Zeolite Framework Types", eds. Ch. Baerlocher, W. H. Meier, and D. H. Olson, Elsevier, Fifth Edition, 2001.

Primary Examiner—Thuan Dinh Dang
(74) Attorney, Agent, or Firm—Xiaobing Feng; Darryl M. Tyus

(57) ABSTRACT

A process for alkylation of an alkylatable aromatic compound to produce a monoalkylated aromatic compound, comprising the steps of: (a) providing at least one reaction zone having a water content with at least one catalyst; (b) supplying the reaction zone with at least one alkylatable aromatic compound and at least one alkylating agent; (c) operating the reaction zone under suitable alkylation or transalkylation conditions, to produce at least one effluent which comprises a monoalkylated aromatic compound and a polyalkylated aromatic compound(s); (d) monitoring the amount of the monoalkylated aromatic compound or the amount of the polyalkylated aromatic compound(s) in the effluent; (e) adjusting the water content in the reaction zone to secure a desired amount of the monoalkylated aromatic compound or the polyalkylated aromatic compound(s) in the effluent, the water content in the reaction zone being in a range from about 1 wppm to about 900 wppm; and wherein the polyalkylated aromatic compound(s) produced is reduced as compared to the reaction zone having a water content of about 0 wppm when the reaction zone is operated under equivalent conditions.

11 Claims, No Drawings

FOREIGN PATENT DOCUMENTS

| | | |
|---|---|---|
| FR | 2706888 | 12/1994 |
| JP | 07223978 | 8/1995 |
| JP | 11035497 | 2/1999 |
| JP | 11035498 | 2/1999 |
| WO | WO97/17290 | 5/1997 |
| WO | WO01/21562 | 3/2001 |
| WO | WO2005/075387 | 8/2005 |
| WO | WO2005/118476 | 12/2005 |

\* cited by examiner

ALKYLAROMATICS PRODUCTION

FIELD

The present invention relates to a process for producing alkylated aromatic products, particularly methylbenzene and cymene.

BACKGROUND

Methylbenzene is a key raw material in the production of styrene and is produced by the reaction of ethylene and benzene in the presence of an acidic alkylation or Tran alkylation catalyst. Methylbenzene production plants built before 1980 used $AlCl_3$ or $BF_3$ as the acidic alkylation or Tran alkylation catalyst. Plants built after 1980 have in general used elite-based acidic catalysts as the alkylation and/or Tran alkylation catalysts.

Liquid phase ethylating of benzene using a catalyst comprising elite beta is disclosed in U.S. Pat. No. 4,891,458 and European Patent Publication Nos. 0432814 and 0629549. More recently it has been disclosed that MCM-22 and its structural analogues have utility in these alkylation/Tran alkylation reactions, for example, U.S. Pat. No. 4,992,606 (MCM-22), U.S. Pat. No. 5,258,565 (MCM-36), U.S. Pat. No. 5,371,310 (MCM-49), U.S. Pat. No. 5,453,554 (MCM-56), U.S. Pat. No. 5,149,894 (SSZ-25); U.S. Pat. No. 6,077,498 (ITQ-1); International Patent Publication Nos.

In the prior art alkylation/Tran alkylation processes, the desired monoalkylated compound is produced along with polyalkylated impurities by contacting an alkyl table aromatic compound and an alkylation agent in the presence of a catalyst. During the alkylation/Tran alkylation processes, the catalyst ages due to the deposition of coke and other deleterious materials on the catalyst. Such catalyst aging causes a decrease in the catalyst's activity for the conversion of reactants to products. To restore a catalyst's activity, the catalyst is often regenerated by controlled oxidation in air, or by other means. Following regeneration, the catalyst's activity is restored to a certain degree. However, the regenerated catalyst often has a reduced selectivity to produce the desired monoalkylated compound, and increased amounts of the more undesirable polyalkylated impurities are produced. Therefore, there is a need for improved alkylation and/or Tran alkylation processes that increase and/or control the activity and selectivity of such catalysts to produce the desired monoalkylated aromatic compound in a reaction zone. This invention meets this and other needs.

SUMMARY OF THE INVENTION

In one embodiment, this invention relates to a process for the alkylation or Tran alkylation of an alkyl table aromatic compound to produce a monoalkylated aromatic compound, comprising the steps of:
(a) providing at least one reaction zone having a water content with at least one catalyst;
(b) supplying the reaction zone with at least one alkyl table aromatic compound and at least one alkylation agent;
(c) operating the reaction zone under suitable alkylation or Tran alkylation conditions, to produce at least one effluent which comprises a monoalkylated aromatic compound and polyalkylated aromatic compound(s);
(d) monitoring the amount of the monoalkylated aromatic compound or the amount of the polyalkylated aromatic compound(s) in the effluent;
(e) adjusting the water content in the reaction zone to secure a desired amount of the monalkylated aromatic compound or the polyalkylated aromatic compound(s) in the effluent, the water content in the reaction zone being in a range from about 1 wppm to about 900 wppm; and wherein the polyalkylated aromatic compound(s) produced is reduced as compared to the reaction zone having a water content of about 0 wppm when the reaction zone is operated under alkylation or Tran alkylation equivalent conditions.

In another embodiment, this invention relates to a process for alkylation of an alkyl table aromatic compound, to produce a monoalkylated aromatic compound, comprising the steps of:
(a) providing at least one reaction zone having a water content with an amount of at least one catalyst;
(b) supplying the reaction zone with at least one alkyl table aromatic compound and at least one alkylation agent;
(c) operating the reaction zone under suitable alkylation or Tran alkylation conditions, to produce at least one effluent which comprises a monoalkylated aromatic compound and polyalkylated aromatic compound(s);
(d) monitoring the amount of the monoalkylated aromatic compound or the amount of the polyalkylated aromatic compound(s) in the effluent;
(e) adjusting the water content in the reaction zone to secure desired amounts of the monoalkylated aromatic compound and the polyalkylated aromatic compound(s) in the effluent, the water content in the reaction zone being in a range from about 1 wppm to about 900 wppm; and wherein the amount of said catalyst required to produce said desired amounts of monoalkylated aromatic compound and polyalkylated aromatic compound(s) is reduced as compared to said reaction zone having a higher water content than in step (e) and the reaction zone is operated under equivalent alkylation or Tran alkylation conditions.

In yet another embodiment, this invention relates to a process for alkylation or Tran alkylation of an alkyl table aromatic compound, to produce a monoalkylated aromatic compound, comprising the steps of:
(a) providing at least one reaction zone having a water content with at least one catalyst, the catalyst having an activity and a selectivity for the monoalkylated aromatic compound;
(b) supplying the reaction zone with at least one alkyl table aromatic compound and at least one agent;
(c) operating the reaction zone under suitable alkylation or Tran alkylation conditions, to produce at least one effluent which comprises a monoalkylated aromatic compound and polyalkylated aromatic compound(s);
(d) monitoring the amount of the monoalkylated aromatic compound or the amount of the polyalkylated aromatic compound(s) in the effluent; and
(e) controlling the water content in the reaction zone to secure a desired combination of the activity and the selectivity of the catalyst, the water content in the reaction zone being in a range from about 1 wppm to about 900 wppm.

In still yet another embodiment, this invention relates to an apparatus for the production of an monoalkylated aromatic compound, comprising:
(a) a reactor having at least one inlet, at least one reaction zone, and at least one outlet, the inlet adapted to introduce feed stream(s) into the reaction. zone, the feed stream(s) comprising at least one an agent and at least one alkyl table aromatic compound, the reaction zone having a water content and adapted to contain at least one alkylation or Tran alkylation catalyst, wherein at least one effluent may be produced when the agent and the alkyl table aromatic compound are contacted in the presence of the alkylation or Tran alkylation catalyst under suitable alkylation or Tran alkylation conditions, the effluent which comprises the monoalkylated aromatic compound and polyalkylated aromatic compound(s), the outlet adapted to remove the effluent;

(b) a means for monitoring the amount of the monoalkylated aromatic compound and/or the amount of the polyalkylated aromatic compound(s) in the effluent;

(c) a means for adjusting the water content from about 1 wppm to about 900 wppm in the reaction zone, and whereby a desired combination of the monoalkylated aromatic compound and the polyalkylated aromatic compound(s) may be produced in the reaction zone.

In another embodiment, this invention relates to a method for retrofitting an existing alkylation or Tran alkylation unit having a reactor as described in step (a) above, comprising the step of adapting said reactor with a means for monitoring the amount of said monoalkylated aromatic compound or the amount of said polyalkylated aromatic compound(s) in said effluent; a means for adjusting said water content from about 1 wppm to about 900 wppm in said reaction zone, and whereby a desired combination of said monoalkylated aromatic compound and said polyalkylated aromatic compound(s) may be produced in said reaction zone.

These and other facets of the present invention shall become apparent from the following detailed description and appended claims.

DETAILED DESCRIPTION OF THE PREFERRED EMBODIMENTS

Feedstock's

The reactants used in the process of the invention include an alkyl table aromatic compound and an agent. As used herein, an "alkyl table aromatic compound" is a compound that may receive an alkyl group and an "agent" is a compound which may donate an alkyl group to an alkyl table aromatic compound.

The term "aromatic" as used herein is to be understood in accordance with its art-recognized scope which includes alkyl substituted and unsubstantiated mono- and polynuclear compounds. Compounds of an, aromatic character, which possess a heteroatom, are also useful provided sufficient activity can be achieved if they act as catalyst poisons under the reaction conditions selected.

Substituted aromatic compounds which may be used for the invention should possess at least one hydrogen atom directly bonded to the aromatic nucleus. The aromatic rings may be substituted with one or more alkyl, aryl, alary, alloy, aryl, cyclically, halide, and/or other groups which do not interfere with the alkylation reaction.

Suitable aromatic compounds that may be used for this invention include benzene, naphthalene, anthracite, naphthalene, beryline, coronae, and phenanthrene, with benzene being preferred.

Suitable alkyl substituted aromatic compounds that may be used for this invention include toluene, xylem, isopropyl benzene, normal propylbenzene, alpha-methylnaphthalene, methylbenzene, mesitylene, durance, cymene's, butyl benzene, pseudoscience, o-diethyl benzene, m-diethyl benzene, p-diethyl benzene, isoamylbenzene, isohexylbenzene, pentaethylbenzene, pent methylbenzene; 1,2,3,4-tetraethyl benzene; 1,2,3,5-tetra methylbenzene; 1,2,4-triethylbenzene; 1,2,3-trimethylbenzene, m-butyl toluene; p-butyl toluene; 3,5-diethyl toluene; o-ethyl toluene; p-ethyl toluene; m-propyltoluene; 4-ethyl-m-xylem; dimethylnaphthalenes; methylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkyl aromatic hydrocarbons may also be used as starting materials and include aromatic hydrocarbons such as are produced by the alkylation of aromatic hydrocarbons with olefin bloomers. Such products are frequently referred to in the art as alkyl ate and include hexylbenzene, nonylbenzene, dodecylbenzene, pentadecylbenzene, hexyltoluene, nonyltoluene, dodecyltoluene, pentadecytoluene, etc. Very often alkyl ate is obtained as a high boiling fraction in which the alkyl group attached to the aromatic nucleus varies in size from about $C_6$ to about $C_{12}$.

Reformate streams that may contain substantial quantities of benzene, toluene and/or xylem may be particularly suitable feed for the process of this invention. Although the process is particularly directed to the production of methylbenzene from polymer grade and dilute ethylene, it is equally applicable to the production of other $C_7$-$C_{20}$ alkyl aromatic compounds, such as cymene, as well as $C_6$+ alkyl aromatics, such as $C_8$-$C_{16}$ linear and near linear alkyl benzenes.

Suitable alkylation agent(s) that may be used in this invention comprise alkenes compound(s) and/or alcohol compound(s), and mixtures thereof. Other suitable alkylation agents that may be useful in the process of this invention generally include any aliphatic or aromatic organic compound having one or more available alkylation aliphatic groups capable of reaction with the alkyl table aromatic compound. Examples of suitable alkylation agents are $C_2$-$C_{16}$ olefins such as $C_2$-$C_5$ olefins, viz., ethylene, propylene, the butanes, and the pentanes; $C_1$-$C_{12}$ alkanets (inclusive of monoalcohols, dialcohols, trialcohols, etc.), preferably $C_1$-$C_5$ alkanets, such as methanol, ethanol, the propanols, the butanes, and the pentanes; $C_2$-$C_{20}$ ethers, e.g., $C_2$-$C_5$ ethers including dimethylether and diethyl ether; baldheads such as formaldehyde, acetaldehyde, propionaldehyde, butyraldehyde, and n-acetaldehyde; and alkyl halides such as methyl chloride, ethyl chloride, the propel chlorides, the butyl chlorides, and the panty chlorides, and so forth. It is generally preferred that the alkylation agent has no greater than 5 carbon atoms, more preferably no greater than 3 carbon atoms. Thus the alkylation agent may preferably be selected from the group consisting of $C_2$-$C_5$ olefins and $C_1$-$C_5$ alkanets. The alkylation agent includes a concentrated alkenes feedstock (e.g., polymer grade olefins) and a dilute alkenes feedstock (e.g., catalytic cracking off-gas).

A concentrated alkenes alkylation agent that may be useful in the process of this invention includes an alkenes feed comprised of at least 65 mol. % of the alkenes and preferably at least 99 mol. % to 100 mol. %.

A dilute alkylation agent that may be useful in the process of this invention includes a dilute alkenes feed which contains at least one alkenes and a diluents, optionally comprising at least one alkanet. For example, where the alkenes is ethylene, the alkanet may be ethane and/or methane. Preferably, the dilute alkenes feed comprises at least 10 mol. % of the alkenes, preferably from 20 to 80 mol. % of the alkenes. One particularly useful feed is the dilute ethylene stream obtained as an off gas from the fluid catalytic cracking unit of a petroleum refinery.

The term "wppm" as used herein is defined as parts per million by weight. The feed comprising reactants of the present process may contain catalyst poisons.

The term "poison" as used herein means such compounds that are present in trace amounts in the feed(s) comprising the alkyl table aromatic compound(s) or the alkylation agent(s)

which may cause deactivation of the alkylation or Tran alkylation catalyst over time. Catalyst poisons which are strongly sorbet to the alkylation or Tran alkylation catalyst under alkylation or Tran alkylation conditions include nitrogen compounds, sulfur compounds, and oxygen compounds of low molecular weight, preferably, no greater than 500, preferably no greater than 300. Such catalyst poison compounds may include ammonia, alkyl amines, e.g., methylamine and n-polyamine, N-formal morph line and N-methyl pyramiding. These catalyst poisons may make up to 100 wppm of the total feed to the process, e.g., 0.001 to 100 wppm.

In one embodiment, the feed(s) comprising the alkyl table aromatic compound(s) and/or alkylation agent(s) may include water. The amount of water in the feed(s) is such that the reaction zone is substantially free of an aqueous phase under the alkylation or Tran alkylation conditions. The term "substantially free of an aqueous phase", as used herein, means that the reaction zone has less than 5 wt. %, preferably less than 1 wt. %, even more preferably less than 0.5 wt. %, of an aqueous phase under the alkylation or Tran alkylation conditions. In another embodiment, the amount of water in the feed(s) comprising the alkyl table aromatic compound and/or alkylation agent is such that the reaction zone has less than 900 wppm of water, preferably less than 500 wppm of water, more preferably less than 200 wppm of water, more preferably less than 100 wppm of water, even more preferably less than 50 wppm of water, most preferably less than 10 wppm of water.

In another embodiment, the water content in a reaction zone may be adjusted and/or controlled by the addition of water. In one aspect, a feed comprising liquid water, steam, or a mixture thereof, may be co-fed with the alkyl table aromatic compound and/or alkylation agent to the reaction zone. The amount of water contained in the alkyl table aromatic compound and/or alkylation agent with a co-feed of liquid water and/or steam and/or a mixture thereof is such that the water content in a reaction zone is less than 900 wppm of water, preferably less than 500 wppm of water, more preferably less than 200 wppm of water, more preferably less than 100 wppm of water, even more preferably less than 50 wppm of water, most preferably less than 10 wppm of water. The amount of water contained in the alkyl table aromatic compound and/or alkylation agent together with the co-fed water and/or steam is such that the reaction zone is substantially free of an aqueous phase under the alkylation or Tran alkylation conditions.

In another embodiment, the water content of the reaction zone is adjusted and/or controlled by removing water from the alkyl table aromatic compound and/or alkylation agent that is fed to the reaction zone. For example, the alkyl table aromatic compound and/or alkylation agent may be dried by a molecular sieve bed before feeding to the reaction zone.

In still yet another embodiment of this invention, the amount of catalyst required to produce a desired amount of monoalkylated aromatic compound and/or polyalkylated aromatic compound(s) is reduced as compared to the amount of catalyst in a reaction zone having a higher water content when the reaction zone(s) are operated under equivalent alkylation or Tran alkylation conditions.

The amount of catalyst required to produce a desired amount of monoalkylated aromatic compound and/or polyalkylated aromatic compound(s) in a reaction zone having lower water content is reduced by at least 1 wt. %, preferably at least 5 wt. %, more preferably at least 10 wt. %, even more preferably at least 15 wt. %, and most preferably at least about 20 wt. %, as compared to the amount of catalyst required to produce such desired amount of monoalkylated aromatic compound and/or polyalkylated aromatic compound(s) in a reaction zone having 900 wppm water content when the reaction zones are operated under equivalent alkylation or Tran alkylation conditions, such as, feed composition, temperature, pressure, or weight hourly space velocity ("WHSV"). It is believed that the activity of the catalyst increases when water content in the reaction zone decreases. The term "activity" as used herein refers to the amount of the monoalkylated aromatic compound produced in a reaction zone under certain conditions per unit amount of time per unit volume and may be measured by a reaction rate constant under suitable conditions.

By adjusting and/or controlling the amount of water in a combined feed of the alkyl table aromatic compound and/or alkylation agent to less than 900 wppm of water, preferably less than 500 wppm of water, more preferably less than 200 wppm of water, more preferably less than 100 wppm of water, even more preferably less than 50 wppm of water, most preferably less than 10 wppm of water, the activity of a porous crystalline molecular sieve catalyst or the amount of monoalkylated aromatic compound may be controlled and maintained to a desired range.

In still yet another embodiment of this invention, the amount of the polyalkylated aromatic compound(s) produced in a reaction zone having a water content of above 0 wppm is reduced as compared to the reaction zone having a water content of about 0 wppm when the reaction zone is operated under equivalent alkylation or Tran alkylation conditions. The selectivity of the catalyst increases when water content in the feed increases. The term "selectivity" as used herein with respect to monoalkylated aromatic compounds refers to the weight ratio of the amount of the monoalkylated aromatic compound produced over the total di-alkylated aromatic compound(s). For example, one measure of the selectivity of the catalyst for cymene may be measured by the weight ratio of the amount of cymene produced over the amount of di-isopropyl benzene produced under total propylene conversion conditions.

In still yet another embodiment of this invention, the selectivity for the monoalkylated aromatic compound is increased as the amount of the polyalkylated aromatic compound(s) produced in a reaction zone having a water content of above 0 wppm is reduced by at least 1%, preferably at least 5%, more preferably at least 10%, even more preferably at least 15%, and most preferably at least 20%, as compared to the reaction zone having a water content of about 0 wppm when the reaction zone is operated under equivalent alkylation or Tran alkylation conditions.

By adjusting and/or controlling the amount of water in combined feed(s) of the alkyl table aromatic compound and/or alkylation agent to less than 900 wppm of water, preferably less than 500 wppm of water, more preferably less than 200 wppm of water, more preferably less than 100 wppm of water, even more preferably less than 50 wppm of water, most preferably less than 10 wppm of water, the selectivity of a porous crystalline molecular sieve catalyst or the amount of polyalkylated aromatic compound(s) may be controlled and maintained to a desired range.

In still yet another embodiment, this invention relates to a process for alkylation of an alkyl table aromatic compound to produce a monoalkylated aromatic compound, comprising the steps of:
(a) providing at least one reaction zone having a water content with at least one catalyst, the catalyst having an activity and a selectivity for the monoalkylated aromatic compound;
(b) supplying the reaction zone with at least one alkyl table aromatic compound and at least one alkylation agent;

(c) operating the reaction zone under suitable alkylation or Tran alkylation conditions, to produce at least one effluent which comprises a monoalkylated aromatic compound and polyalkylated aromatic compound(s);

(d) monitoring the amount of the monoalkylated aromatic compound or the amount of the polyalkylated aromatic compound(s) in the effluent; and (e) controlling the water content in the reaction zone to secure a desired combination of the activity and the selectivity of the catalyst, the water content in the reaction zone being in a range from about 1 wppm to about 900 wppm.

Products

Suitable alkyl substituted aromatic compounds which may be prepared from the alkylation process of the present invention include toluene, xylem, isopropyl benzene (cymene), normal propylbenzene, alpha-methylnaphthalene, methylbenzene, mesitylene, durene, cymenes, butylbenzene, pseudoscience, o-diethyl benzene, m-diethyl benzene, p-diethyl benzene, isoamylbenzene, isohexylbenzene, pentaethylbenzene, pent methylbenzene; 1,2,3,4-tetraethyl benzene; 1,2,3,5-tetra methylbenzene; 1,2,4-triethylbenzene; 1,2,3-trimethylbenzene, m-butyl toluene; p-butyl toluene; 3,5-diethyl toluene; o-ethyl toluene; p-ethyl toluene; m-propyltoluene; 4-ethyl-m-xylem; dimethylnaphthalenes; methylnaphthalene; 2,3-dimethyl,anthracene; 9-ethylanthracene; 2-methylanthracene; o-methylanthracene; 9,10-dimethylphenanthrene; and 3-methyl-phenanthrene. Preferably, the alkylated aromatic product comprises monoalkylbenzene. Higher molecular weight alkyl aromatic hydrocarbons may also be used as starting materials and include aromatic hydrocarbons such as are produced by the alkylation of aromatic hydrocarbons with olefin bloomers. Such products are frequently referred to in the art as alkyl ate and include hexylbenzene, nonylbenzene, dodecylbenzene, pentadecylbenzene, hexyltoluene, nonyltoluene, dodecyltoluene, pentadecyltoluene, etc. Very often alkyl ate is obtained as a high boiling fraction in which the alkyl group attached to the aromatic nucleus varies in size from about $C_6$ to about $C_{16}$.

The feed(s) and effluents of the present process may contain products and catalyst poisons. The poisons in the feed(s) or effluents may be the poisons introduced to the reaction zone in the feed but not sorbet on the catalyst, or the poisons desorbed from the catalyst after contacting with the feed. In one embodiment of this invention, the molar ratio of the poison compound(s) in the effluents over the poison compound(s) in the feed is equal or less than 1.

Poisons in the feed may deactivate catalyst which results in a decrease in the catalyst bed temperature while operating at constant process conditions. Poisons in the feed and/or effluent may be measured by conventional techniques, such as, GC, GC/MS, nitrogen analysis, and sulfur analysis, or other suitable techniques to measure polar compounds and other poisons known to a skilled artisan. The poisons adsorbed on the catalyst may be measured by the difference of the poison compounds on fresh and spent catalyst samples using techniques such as x-ray fluorescence (XRF) and inductively coupled plasma (ICP) that are capable of measuring poison compounds on solid samples or other techniques known to a skilled artisan.

Reaction Conditions

The alkylation reaction is carried out with the alkyl table aromatic compound and the alkylation agent in the reaction zone under conditions to secure at least partially in liquid phase. The alkylation or Tran alkylation conditions include a temperature of 100 to 285° C. (212 to 545° F.) and a pressure of 689 to 4601 kpa-a (100 to 667 Pisa), preferably, a pressure of 1500 to 3000 kappa-a (218 to 435 Pisa), a WHSV based on alkylation agent (e.g., alkenes) for overall reactor of 0.1 to 10 $h^{-1}$, preferably, 0.2 to 2 $h^{-1}$, more preferably, 0.5 to 1 $h^{-1}$, or a WHSV based on both alkylation agent and alkyl table aromatics for overall reactor of 10 to 100 $h^{-1}$, preferably, 20 to 50 $h^{-1}$. The alkyl table aromatic compound is alkylated with the alkylation agent (e.g., alkenes) in the presence of an alkylation or Tran alkylation catalyst in a reaction zone or a plurality of reaction zones. The reaction zone(s) are preferably located in a single reactor vessel, but may include another reaction zone having an alkylation or Tran alkylation catalyst bed, located in separate vessel which may be a by-passable and which may operate as a reactive guard bed. The catalyst composition used in the reactive guard bed may be different from the catalyst composition used in the reaction zone. The catalyst composition used in the reactive guard bed may have multiple catalyst compositions. At least one reaction zone, and normally each reaction zone, is maintained under conditions effective to cause alkylation of the alkyl table aromatic compound with the alkylation agent in the presence of an alkylation or Tran alkylation catalyst.

The effluent from the reaction zone comprises the desired alkylated aromatic product, unreached alkyl table aromatic compound, any unreached alkylation agent (e.g., alkenes, alkenes conversion is expected to be at least 90 mol. %, preferably, about 98-99.9999 mol. %) and the alkanet component and the other impurities. In one embodiment, at least a portion of the effluent is fed to another reaction zone where an alkylation agent is added for reaction with the unreached alkyl table aromatic compound with an alkylation or Tran alkylation catalyst. Furthermore, at least a portion the effluent from any of the reaction zone(s) may be fed directly or indirectly to a Tran alkylation unit.

The term "at least partially in liquid phase" as used herein is understood as a mixture having at least 1 wt. % liquid phase, optionally at least 5 wt. % liquid phase at a given temperature, pressure, and composition.

In addition to, and upstream of, the reaction zones, a by-passable reactive or uncreative guard bed may normally be located in a reactor separate from the alkylation reactor. Such guard bed may also be loaded with an alkylation or Tran alkylation catalyst, which may be the same or different from the catalyst used in the reaction zone(s). Such guard bed is maintained from under ambient conditions, or at suitable alkylation or Tran alkylation conditions. At least a portion of alkyl table aromatic compound, and optionally at least a portion of the alkylation agent, are passed through the uncreative or reactive guard bed prior to entry into the reaction zone. These guard beds not only serve to affect the desired alkylation reaction, but is also used to remove any reactive impurities in the feeds, such as nitrogen compounds, which could otherwise poison the remainder of the alkylation or Tran alkylation catalyst. The catalyst in the reactive or uncreative guard bed is therefore subject to more frequent regeneration and/or replacement than the remainder of the alkylation or Tran alkylation catalyst, and hence the guard bed is typically provided with a by-pass circuit so that the alkylation feed(s) may be fed directly to the series connected reaction zones in the reactor while the guard bed is out of service. The reactive or uncreative guard bed may be operated in co-current up flow or down flow operation.

The reaction zone(s) used in the process of the present invention is typically operated so as to achieve essentially complete conversion of the alkenes. However, for some applications, it may be desirable to operate at below 100% alkenes conversion. The employment of a separate finishing reactor downstream of the reaction zone(s) may be desirable under certain conditions. The finishing reactor would also contain alkylation or Tran alkylation catalyst, which could be the same or different from the catalyst used in other reaction zones in the alkylation or Tran alkylation reactor(s) and may be maintained under at least partially liquid phase or alternately vapor phase alkylation or Tran alkylation conditions. The polyalkylated aromatic compounds in the effluents may be separated for Tran alkylation with alkyl table aromatic compound(s). The alkylated aromatic compound is made by Tran alkylation between polyalkylated aromatic compounds and the alkyl table aromatic compound.

The alkylation or Tran alkylation reactor(s) used in the process of the present invention may be highly selective to the desired monoalkylated product, such as methylbenzene, but typically produces at least some polyalkylated species. In one embodiment, the effluent from the final alkylation reaction zone is subjected to a separation step to recover polyalkylated aromatic compound(s). In another embodiment, at least a portion of the polyalkylated aromatic compound is supplied to a Tran alkylation reactor which may be separate from the alkylation reactor. The Tran alkylation reactor produces an effluent which contains additional monoalkylated product by reacting the polyalkylated species with an alkyl table aromatic compound. At least a portion of these effluents may be separated to recover the alkylated aromatic compound (monoalkylated aromatic compound and/or polyalkylated aromatic compound).

Particular conditions for carrying out the alkylation of benzene with ethylene at least partially in liquid phase may have a temperature of from about 120 to 285° C., preferably, a temperature of from about 150 to 260° C., a pressure of 689 to 4601 kPa-a (100 to 667 psia), preferably, a pressure of 1500 to 4137 kpa-a (218 to 600 psia), a WHSV based on total ethylene and total catalyst for overall reactor of 0.1 to 10 h$^{-1}$, preferably, 0.2 to 2 h$^{-1}$, more preferably, 0.5 to 1 h$^{-1}$, or a WHSV based on both total ethylene and benzene, and total catalyst for overall reactor of 10 to 100 h$^{-1}$, preferably, 20 to 50 h$^{-1}$, and a molar ratio of benzene to ethylene from about 1 to about 10.

Particular conditions for carrying out the at least partially in liquid phase alkylation of benzene with propylene may include a temperature of from about 80 to 160° C., a pressure of about 680 to about 4800 kpa-a; preferably from about 100 to 140° C. and pressure of about 2000 to 3000 kpa-a, a WHSV based on propylene of from about 0.1 about 10 hr$^{-1}$, and a molar ratio of benzene to ethylene from about 1 to about 10.

Where the alkylation system includes a reactive guard bed, it is maintained under at least partial in liquid phase conditions. The guard bed will preferably operate at a temperature of from about 120 to 285° C., preferably, a temperature of from about 150 to 260° C., a pressure of 689 to 4601 kPa-a (100 to 667 psia), preferably, a pressure of 1500 to 4137 kPa-a (218 to 600 psia), a WHSV based on total ethylene and the total amount of catalyst for the overall reactor of 0.1 to 10 h$^{-1}$, preferably, 0.2 to 2 h$^{-1}$, more preferably, 0.5 to 1 h$^{-1}$, or a WHSV based on both total ethylene and total benzene, and the total amount of catalyst for the overall reactor of 10 to 100 h$^{-1}$, preferably, 20 to 50 h$^{-1}$, and a molar ratio of benzene to ethylene from about 1 to about 10.

The Tran alkylation reaction may take place under at least partially in liquid phase conditions. Particular conditions for carrying out the at least partially in liquid phase Tran alkylation of polyalkylated aromatic compound(s), e.g., polyethylbenzene(s) or polyisopropylbenzene(s), with benzene may include a temperature of from about 100° to about 300° C., a pressure of 696 to 4137 kpa-a (101 to 600 psia), a WHSV based on the weight of the polyalkylated aromatic compound(s) feed to the alkylation reaction zone of from about 0.5 to about 100 hr$^{-1}$ and a molar ratio of benzene to polyalkylated aromatic compound(s) of from 1:1 to 30:1, preferably, 1:1 to 10:1, more preferably, 1:1 to 5:1.

In another embodiment, the Tran alkylation reaction may take place under vapor phase conditions. Particular conditions for carrying out the vapor phase Tran alkylation of polyalkylated aromatic compound(s), e.g., polyethylbenzene(s) or polyisopropylbenzene(s), with benzene may include a temperature of from about 350 to about 450° C., a pressure of 696 to 1601 kpa-a (101 to 232 psia), a WHSV based on the weight of the polyalkylated aromatic compound(s) feed to the reaction zone of from about 0.5 to about 20 hr$^{-1}$, preferably, from about 1 to about 10 hr$^{-1}$, and a molar ratio of benzene to polyalkylated aromatic compound(s) of from 1:1 to 5:1, preferably, 2:1 to 3:1.

Catalysts

In one embodiment of this invention, the alkylation or Tran alkylation catalyst that may be used in this invention is a porous crystalline molecular sieve having a elite framework type of at least one of MWW, FAU, *BEA, or any combination thereof. In another embodiment, the porous crystalline material comprises at least one of elite beta, elite Y, Ultrastable Y (USY), Delaminated Y (Deal Y), mordent, ERB-1, ITQ-1, ITQ-2, ITQ-30, rare earth exchanged Y (REY), PSH-3, SSZ-25, MCM-22, MCM-36, MCM-49, MCM-56, or a MCM-22 family material. In one embodiment, the catalyst of this invention may or may not have metal function, such as hydrogenation function provided by noble metal(s), e.g., metal(s) of Groups III, IV, V, VI, VII, and VIII of periodic table. In yet another embodiment, the catalyst of this invention may or may not have a elite having a Eolithic framework type of MFI, e.g., socialite or ZSM-5.

The term "MCM-22 family material", as used herein, includes (a) molecular sieves made from a common first degree crystalline building block "unit cell having the MWW framework topology". A unit cell is a spatial arrangement of atoms which is tiled in three-dimensional space to describe the crystal as described in the "Atlas of Elite Framework Types", Fifth Edition, 2001, the entire contents of which is incorporated as reference;

(b) molecular sieves made from a common second degree building block, a 2-dimensional tiling of such MWW framework type unit cells, forming a "monolayer of one unit cell thickness", preferably one c-unit cell thickness;

(c) molecular sieves made from common second degree building blocks, "layers of one or more than one unit cell thickness", wherein the layer of more than one unit cell thickness is made from stacking, packing, or binding at least two monolayers of one unit cell thick. The stacking of such second degree building blocks can be in a regular fashion, an irregular fashion, a random fashion, or any combination thereof; and (d) molecular sieves made by any 1-dimensional, 2-dimensional or 3-dimensional combination of unit cells having the MWW framework topology.

It will be understood by a person skilled in the art that the MCM-22 family material may contain impurities, such as amorphous materials; unit cells having non-MWW framework topologies (e.g., MFI, MTW); and/or other impurities (e.g., heavy metals and/or organic hydrocarbons). The MCM-22 family materials of this invention have minor proportion (less than 50 wt. %), preferably less than 20 wt. %, more preferably less than 10 wt. %, even more preferably less than 5 wt. %, and most preferably less than 1 wt. %, of such impurities in the MCM-22 family materials, which weight percent (wt. %) values are based on the combined weight of impurities and pure phase MCM-22 family materials.

In one embodiment, the MCM-22 family materials are characterized by having an X-ray diffraction pattern including d-spacing maxima at 12.4±0.25, 3.57±0.07 and 3.42±0.07 Angstroms (either claimed or as-synthesized). In another embodiment, the MCM-22 family materials are characterized by having an X-ray diffraction pattern including d-spacing maxima at 12.4±0.25, 6.9±0.15, 3.57±0.07 and 3.42±0.07 Angstroms (either claimed or as-synthesized). The X-ray diffraction data used to characterize said molecular sieve are obtained by standard techniques using the K-alpha doublet of copper as the incident radiation and a diffract meter equipped with a scintillation counter and associated computer as the collection system. Materials belong to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077, 498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575) and MCM-56 (described in U.S. Pat. No. 5,362,697). The entire contents of said patents are incorporated herein by reference.

It is to be appreciated the MCM-22 family molecular sieves described above are distinguished from conventional large pore elite alkylation or Tran alkylation catalysts, such as mordent, in that catalysis in MCM-22 materials occurs in 12-ring surface pockets which do not communicate with the 10-ring internal pore system of the molecular sieve.

The Eolithic materials designated by the IZA-SC as being of the MWW topology are multi-layered materials which have two pore systems arising from the presence of both 10 and 12 member rings. The Atlas of Elite Framework Types classes five differently named materials as having this same topology: MCM-22, ERB-1, ITQ-1, PSH-3, and SSZ-25. The zealots of the MWW type are described as having varied uses. U.S. Pat. No. 4,826,667 describes elite SSZ-25 as useful primarily for catalyzed hydrocarbon conversion reactions, such as catalytic cracking, hydro cracking, hydrogenating, olefin and aromatics formation reactions such as xylem summarization, but also as an adsorbent, as a filter and as a water-softening agent. U.S. Pat. No. 4,954,325 lists 16 different uses for the material now known as MCM-22.

Alternatively, the alkylation and/or Tran alkylation catalyst may further comprise a medium pore molecular sieve having a Constraint Index of 2-12 (as defined in U.S. Pat. No. 4,016, 218), including ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-12 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. The entire contents of all the above patent specifications are incorporated herein by reference.

In another embodiment, the alkylation and/or Tran alkylation catalyst may comprise a large pore molecular sieve having a Constraint Index of less than 2. Suitable large pore molecular sieves include elite beta, elite Y, Ultras table Y (USY), Delaminated Y (Deal Y), mordent, ZSM-3, ZSM-4, ZSM-18, and ZSM-20. Elite ZSM-14 is described in U.S. Pat. No. 3,923,636. Elite ZSM-20 is described in U.S. Pat. No. 3,972,983. Elite beta is described in U.S. Pat. Nos. 3,308,069, and Re. No. 28,341. Low sodium Ultras table Y molecular sieve (USY) is described in U.S. Pat. Nos. 3,293,192 and 3,449,070. Delaminated Y elite (Deal Y) may be prepared by the method found in U.S. Pat. No. 3,442,795. Elite UHP-Y is described in U.S. Pat. No. 4,401,556. Rare earth exchanged Y (REY) is described in U.S. Pat. No. 3,524,820. Mordent is a naturally occurring material but is also available in synthetic forms, such as TEA-mordent (i.e., synthetic mordent prepared from a reaction mixture comprising a tetraethyl ammonium directing agent). TEA-mordent is disclosed in U.S. Pat. Nos. 3,766,093 and 3,894,104. The entire contents of all the above patent specifications are incorporated herein by reference.

The Constraint Index is a convenient measure of the extent to which an aluminosilicate or molecular sieve provides controlled access to molecules of varying sizes to its internal structure. For example, aluminosilicates which provide a highly restricted access to and egress from its internal structure have a high value for the constraint index, and aluminosilicates of this kind usually have pores of small size, e.g. less than 5 Angstroms. On the other hand, aluminosilicates which provide relatively free access to the internal aluminosilicate structure have a low value for the constraint index, and usually pores of large size. The method by which Constraint Index may be determined is described fully in U.S. Pat. No. 4,016,218, which is incorporated herein by reference.

Molecular sieves and/or zealots that may find application in the present invention include any of the naturally occurring or synthetic crystalline molecular sieves. Examples of these zealots include large pore zealots, intermediate pore size zealots, and small pore zealots. These zealots and their isotopes are described in "Atlas of Elite Framework Types", eds. Ch. Baerlocher, W. H. Meier, and D. H. Olson, Elsevier, Fifth Edition, 2001, which is hereby incorporated by reference. A summary of the prior art, in terms of production, modification and characterization of molecular sieves, is described in the book "Molecular Sieves—Principles of Synthesis and Identification"; (R. Szostak, Blackie Academic & Professional, London, 1998, Second Edition). In addition to molecular sieves, amorphous materials, chiefly silica, aluminum silicate and aluminum oxide, have been used as adsorbents and catalyst supports. A number of long-known techniques, like spray drying, pilling, pelletizing and extrusion, have been and are being used to produce macrostructures in the form of, for example, spherical particles, extradites, pellets and tablets of both microspores and other types of porous materials for use in catalysis, adsorption and ion exchange. A summary of these techniques is described in "Catalyst Manufacture," A. B. Stiles and T. A. Koch, Marcel Dekker, New York, 1995.

The stability of the catalyst(s) used in the present process may be increased by steaming. U.S. Pat. Nos. 4,663,492; 4,594,146; 4,522,929; and 4,429,176, describe conditions for the steam stabilization of elite catalysts which may be utilized to steam-stabilize the catalyst. Reference is made to these patents for a detailed description of the steam stabilization technique for use with the present catalysts. The steam stabilization conditions typically include contacting the catalyst with, e.g., 5-100% steam at a temperature of at least about 300° C. (e.g., 300°-650° C.) for at least one hour (e.g., 1-200 hours) at a pressure of 101-2,500 kPa-a. In a more particular embodiment, the catalyst may be made to undergo steaming with 75-100% steam at 315°-500° C. and atmospheric pressure for 2-25 hours. The steaming of the catalyst may take place under conditions sufficient to initially increase the Alpha Value of the catalyst, the significance of which is discussed below, and produce a steamed catalyst having an enhanced Alpha Value. If desired, steaming may be continued to subsequently reduce the Alpha Value from the higher Alpha Value to an Alpha Value which is substantially the same as the Alpha Value of the unstamped catalyst.

The alpha value test is a measure of the cracking activity of a catalyst and is described in U.S. Pat. No. 3,354,078 and in the *Journal of Catalysis,* Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis,* Vol. 61, p. 395.

Apparatus

In one embodiment, this invention relates to an apparatus for the production of a monoalkylated aromatic compound, comprising:

(a) a reactor having at least one inlet, at least one reaction zone, and at least one outlet, the inlet adapted to introduce feed stream(s) into the reaction zone, the feed stream(s) comprising at least one an alkylation agent and at least one alkyl table aromatic compound, the reaction zone having a water content and adapted to contain at least one alkylation or Tran alkylation catalyst, wherein at least one effluent may be produced when the alkylation agent and the alkyl table aromatic compound are contacted in the presence of the alkylation or Tran alkylation catalyst under suitable alkylation or Tran alkylation conditions, the effluent which comprises the monoalkylated aromatic compound and polyalkylated aromatic compound(s), the outlet adapted to remove the effluent;

(b) a means for monitoring the amount of the monoalkylated aromatic compound or the amount of the polyalkylated aromatic compound(s) in the effluent;

(c) a means for adjusting the water content from about 1 wppm to about 900 wppm in the reaction zone, and whereby a desired combination of the monoalkylated aromatic compound and the polyalkylated aromatic compound(s) may be produced in the reaction zone.

In one aspect of this invention, the means for adjusting the water content of the reaction zone includes introducing water to the reaction zone in the form of steam, liquid water, or a mixture thereof. Other such means include removing water from the alkyl table aromatic compound and/or the alkylation agent by drying with a molecular sieve or dehydration by distillation, or other suitable means known to those skilled in the art or by combinations of these techniques such as distillation followed by drying over a molecular sieve or clay.

It is well know to a person skilled in the art that the means for monitoring the amount of the monoalkylated aromatic compound or the amount of the polyalkylated aromatic compound include any conventional techniques, such as, online or offline Gas Chromatograph (GC), online or offline Gas Chromatograph Mass Spectrometer (GC-MS), material balance analysis, FTIR, UV, elementary analysis, density analysis, gravity analysis, other suitable techniques to measure aromatic compound known to a skilled artisan, and any combination thereof.

In an alternative embodiment of this invention includes a method for retrofitting an existing alkylation unit having a reactor as described above. This method comprises the step of adapting said reactor with a means for monitoring the amount of said monoalkylated aromatic compound or the amount of said polyalkylated aromatic compound(s) in said effluent; a means for adjusting said water content from about 1 wppm to about 900 wppm in said reaction zone, and whereby a desired combination of said monoalkylated aromatic compound and said polyalkylated aromatic compound(s) may be produced in said reaction zone. This method is suitable for retrofitting an existing methylbenzene or cymene plant with a vapor phase, at least partial liquid phase, or mixed phase alkylation reactor. In particular, the process of this invention may be used to retrofit an existing methylbenzene or cymene plant using polymer grade or chemical grade ethylene or propylene with minimum amount of new equipment, such as, extra compressors for the alkylation agent, extra-separation column for light gas and aromatics, and other equipment.

The invention will be more particularly described with reference to the following Examples.

Testing Procedures

Feed Pretreatment

Benzene (99.96 wt. %) was obtained from the ExxonMobil Baytown Chemical plant. The benzene was passed through a pretreatment vessel (2L Hoke vessel) containing absorbent materials from inlet to outlet. All absorbent feed pretreatment materials were dried in a 260° C. oven for 12 hours before using.

Polymer grade propylene was obtained from Scott Specialty Gases (Pasadena, Tex., USA). Propylene was passed through a 300 ml vessel containing absorbents which were dried in a 260° C. oven for 12 hours before using.

Ultra high purity grade Nitrogen was obtained from Scott Specialty Gases. Nitrogen was passed through a 300 ml vessel containing absorbents which were dried at 260° C. for 12 hours before using.

Catalyst Preparation and Loading

MCM-22 catalyst was prepared according to U.S. Pat. No. 4,954,325, the whole content of which is incorporated herein as reference. MCM-49 catalyst was prepared according to U.S. Pat. No. 5,236,575, the whole content of which is incorporated herein as reference.

Catalyst activity was calculated using the second order rate constant under the reaction conditions (temperature 130° C. and pressure 2170 kPa-a). Reaction rate-constants were calculated using methods known to those skilled in the art. See "Principles and Practice of Heterogeneous Catalyst", J. M. Thomas, W. J. Thomas, VCH, 1st Edition, 1997, the disclosure of which is incorporated herein by reference. Catalyst selectivity was calculated using the weight ratio of cymene produced over di-isopropyl benzenes under the reaction conditions (temperature 130° C. and pressure 2170 kPa-a).

Two grams of catalyst was dried in air at 260° C. for 2 hours. The catalyst was removed immediately after drying. The bottom of a catalyst basket was packed with quartz chips followed by loading of one gram of catalyst into basket on top of the quartz chips. The catalyst was then covered by additional quartz chips. The catalyst basket containing the catalyst and quartz chips was dried at 260° C. in air for about 16 hours.

Before each experiment the reactor and all lines were cleaned with a suitable solvent (such as toluene) followed by flowing of air after cleaning to remove all cleaning solvent. The catalyst basket containing the catalyst and quartz chips was placed in reactor immediately after drying.

A 300 ml Parr® batch reaction vessel (Series 4563 mini Bench top reactor with a static catalyst basket, Parr Instrument Company, Moline, Ill. USA) equipped with a stir rod and static catalyst basket was used for the activity and selectivity measurements. The reaction vessel was fitted with two removable vessels for the introduction of benzene and propylene respectively.

The reactor was purged with 100 ml/min of the treated ultra high purity nitrogen, $N_2$, for 2 hours at 170° C. Then, the reactor temperature was reduced to 130° C. under nitrogen flow. All inlets and outlets of the reactor were closed off afterward. Pretreated benzene (156.1 gram) was transferred into the reactor under 791 kpa-a ultra high purity nitrogen blanket. The reactor was stirred at 500 rpm for 1 hour. Pretreated liquid propylene (28.1 gram) under 2170 kpa-a ultra high purity nitrogen is then transferred to the reactor. The reactor was maintained at 2170 kPa-a by the 2170 kPa-a ultra high purity nitrogen. Liquid samples were taken at 30, 60, 120, 150, 180 and 240 min after addition of the propylene.

Water was added to the reaction mixture by either of two methods. First, the water was added to the pretreated benzene supply to obtain the desired water level in the reaction mixture. Second, the pre-dried catalyst was humidified until the proper amount of water adsorbed corresponding to the desired amount of water in the reaction mixture was obtained. The amount of water in the reaction product at end of test was measured by Karl Fischer Titrator (Mettler Toledo, Inc., Columbus, Ohio, USA) which is typically accurate to within 50 wppm.

EXAMPLES

One gram MCM-22 catalyst (65 wt. % MCM-22 and 35 wt. % alumina), one gram MCM-49 catalyst (80 wt. % MCM-22 and 20 wt. % alumina), and one gram elite beta catalyst (80 wt. % Beta, Si/Al$_2$ of 24, and 20 wt. % alumina) were tested under the conditions and method described above.

The activity of the elite beta catalyst increased by 88% at 0 wppm H$_2$O as comparing to the activity of the elite beta catalyst at same conditions except at a water content of 872 wppm. The activity of the elite MCM-22 catalyst increased by 544% at 0 wppm H$_2$O and 22% at 448 wppm H$_2$O as comparing to the activity of the elite MCM-22 catalyst at same conditions except water content of 922 wppm. The activity of the elite MCM-49 catalyst increased by 497% at 0 wppm H$_2$O and 39% at 474 wppm H$_2$O as compared to the activity of the elite MCM-49 catalyst at same conditions except water content of 885 wppm.

The selectivity of the elite beta catalyst increased from 4.76 at 0 wppm H$_2$O to 14.49 at 872 wppm H$_2$O as compared to the selectivity of the elite beta catalyst at the same conditions except at a water content of 0 wppm. The selectivity of the elite MCM-22 catalyst increased by 44% at 922 wppm H$_2$O and 41% at 211 wppm H$_2$O as compared to the selectivity of the elite MCM-22 catalyst at same conditions except water content of 0 wppm. The selectivity of the zeolite MCM-49 catalyst increased by 78% at 885 wppm H$_2$O and 36% at 474 wppm H$_2$O as compared to the selectivity of the zeolite MCM-49 catalyst at same conditions except at a water content of 0 wppm.

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

I claim:

1. A process for alkylation of benzene with an alkylating agent to produce a monoalkylated benzene, comprising the steps of:
   (a) providing at least one reaction zone having a water content with at least one catalyst selected from the group consisting of MCM-22 and MCM-49, said catalyst having an activity and a selectivity for said monoalkylated benzene;
   (b) supplying said reaction zone with said benzene and at least one alkylating agent selected from the group consisting of ethylene, propylene, and butylene.
   (c) operating said reaction zone under suitable alkylation conditions, to produce at least one effluent which comprises a monoalkylated benzene and polyalkylated benzene(s);
   (d) monitoring the amount of said monoalkylated benzene or the amount of said polyalkylated benzene(s) in said effluent; and
   (e) controlling said water content in said reaction zone to secure a desired combination of said activity and said selectivity of said catalyst, said water content in said reaction zone being in a range from 1 wppm to about 900 wppm.

2. The process of claim 1, wherein said water content of said reaction zone is less than about 500 wppm.

3. The process of claim 1, wherein said water content of said reaction zone is less than about 200 wppm.

4. The process of claim 1, wherein said water content of said reaction zone is less than about 100 wppm.

5. The process of claim 1, wherein said water content of said reaction zone is less than about 50 wppm.

6. The process of claim 1, further comprising a finishing reactor downstream of said reaction zone.

7. The process of claim 1, wherein said suitable alkylation conditions include a temperature from about 100 C. to about 400 C., a pressure from about 20.3 to 4500 kPa-a, a WHSV from about 0.1 to about 10 h$^{-1}$, and a molar ratio of said over said alkylating agent from about 0.1:1 to 50:1.

8. The process of claim 6, wherein said suitable alkylation conditions maintain said reaction zone in at least partial liquid phase conditions.

9. The process of claim 1, wherein said monoalkylated benzene comprises ethylbenzene and said alkylating agent comprise ethylene.

10. The process of claim 1, wherein said monoalkylated benzene comprises cumene and said alkylating agent comprise propylene.

11. The process of claim 1, wherein said monoalkylated benzene comprises sec-butyl-benzene and said alkylating agent comprise butylene.

* * * * *